US007815878B1

(12) United States Patent
Wheatley

(10) Patent No.: US 7,815,878 B1
(45) Date of Patent: Oct. 19, 2010

(54) AROMATHERAPY PUFFER BALL

(75) Inventor: Alan J. Wheatley, Draper, UT (US)

(73) Assignee: American Covers, Inc., BluffDale, UT (US)

( * ) Notice: Subject to any disclaimer, the term of this patent is extended or adjusted under 35 U.S.C. 154(b) by 630 days.

(21) Appl. No.: 11/896,000

(22) Filed: Aug. 27, 2007

Related U.S. Application Data

(60) Provisional application No. 60/841,054, filed on Aug. 29, 2006.

(51) Int. Cl.

| | |
|---|---|
| ***A61L 9/00*** | (2006.01) |
| ***A62B 7/08*** | (2006.01) |
| ***A24F 25/00*** | (2006.01) |
| ***B65D 1/32*** | (2006.01) |
| ***B65D 9/00*** | (2006.01) |
| ***B65D 85/20*** | (2006.01) |
| ***A61H 15/00*** | (2006.01) |
| ***A61H 19/00*** | (2006.01) |
| ***A63B 55/00*** | (2006.01) |
| ***B65B 53/00*** | (2006.01) |
| ***B65B 11/52*** | (2006.01) |
| ***B65B 11/00*** | (2006.01) |

(52) U.S. Cl. ............................... 422/306; 422/1; 422/5; 422/120; 422/123; 239/34; 239/326; 239/56; 239/327; 601/131; 601/134; 601/136; 216/DIG. 88; 221/312 C; 206/315.1; 206/315.2; 206/315.9; 206/528; 206/439; 206/484; 206/497; 53/461; 53/463; 53/476; 53/48.3; 53/509

(58) Field of Classification Search ..................... 422/1, 422/5, 120, 123, 306; 239/34, 326, 56, 327; 601/131, 134, 136; 261/DIG. 88; 221/312 C; 206/315.1, 315.2, 315.9, 528, 439, 484, 497; 53/461, 463, 476, 48.3, 509

See application file for complete search history.

(56) References Cited

U.S. PATENT DOCUMENTS

| | | | | |
|---|---|---|---|---|
| 2,025,657 | A * | 12/1935 | Ganz | 239/55 |
| 4,858,831 | A | 8/1989 | Spector | |
| 4,889,284 | A | 12/1989 | Spector | |
| 5,026,054 | A * | 6/1991 | Osher et al. | 473/594 |
| 5,109,029 | A | 4/1992 | Malone | |
| 5,284,272 | A | 2/1994 | Wei | |
| 5,334,361 | A | 8/1994 | Rafaelides et al. | |
| 5,520,617 | A | 5/1996 | Wei | |

(Continued)

OTHER PUBLICATIONS

Therapeutic Benefits of TheraSqueeze with Aroma Therapy, aromatherasqueeze.com, 1 page.
Manage and measure your stress, Aroma Dough Stress Squeezer, www.stress.org.uk/4560/26866.html, 13 pages.
Hacky Kat Aromatherapy Stress Ball by Kooky Kat, Plain Brown tabby Toys and Treats, 2002-2006, 3 pages.

*Primary Examiner*—Jill Warden
*Assistant Examiner*—Monzer R Chorbaji
(74) *Attorney, Agent, or Firm*—Thorpe North & Western, LLP

(57) ABSTRACT

An air freshener device includes an open-cell, polyurethane foam body having a scent material interspersed in the foam body that is capable of diffusing out of the foam, and a flexible cover surrounding and conforming to the foam body having at least one hole in the cover to facilitate the release of scent. The foam body can be flexible and compressible, and also resilient and returnable to its original configuration. The flexible cover can have a fabric shell that is soothing to the touch, and may also have a non-porous inner liner to contain the scent material and prevent it from migrating out of the foam body. In addition, the air freshener can have a freestanding, self-supported, three-dimensional shape, and can be fashioned into the shape of a common sports ball, such as a baseball.

25 Claims, 4 Drawing Sheets

U.S. PATENT DOCUMENTS

| | | | |
|---|---|---|---|
| 5,690,586 | A | 11/1997 | Wilhelm |
| 5,830,109 | A | 11/1998 | Juarez |
| 5,965,182 | A | 10/1999 | Lindgren |
| 6,224,513 | B1 | 5/2001 | Chow |
| 6,475,119 | B2 | 11/2002 | Chow |
| 6,736,335 | B2 | 5/2004 | Cuthbert |
| 6,905,431 | B2 | 6/2005 | Pearce et al. |
| 7,041,769 | B2 * | 5/2006 | Wu et al. .................... 528/61 |
| 7,637,229 | B2 * | 12/2009 | Hurwitz et al. ............. 119/171 |
| 2003/0213440 | A1 * | 11/2003 | Kelly ......................... 119/708 |
| 2004/0009846 | A1 | 1/2004 | Smirh |
| 2005/0283100 | A1 | 12/2005 | Whittier |

* cited by examiner

AROMATHERAPY PUFFER BALL

RELATED APPLICATIONS

This application claims priority to U.S. Provisional Patent Application No. 60/841,054, filed Aug. 29, 2006, in the United States Patent and Trademark Office, and entitled, “Aroma Therapy Puffer Ball,” which application is incorporated by reference in its entirety herein.

FIELD OF THE INVENTION

The present invention relates generally to air fresheners, and more specifically to small, portable air fresheners for the home, office or car.

BACKGROUND OF THE INVENTION AND RELATED ART

Air fresheners are common devices used to improve and/or change the olfactory characteristics of a localized environment. Such environments can include bathrooms or wash closets, vehicles, lockers, drawers, etc. Such air fresheners typically include a scent that is aesthetically pleasing, such as flowers, fruits, etc.

One common type of air freshener is a two-dimensional, paper-fiber card with a fragrance surrounded in a clear plastic envelope. The envelope is pierced to form an opening, and a portion of the freshener protrudes through the opening to release a scent. The air freshener includes a string or elastic forming a loop to suspend the air freshener. Such air fresheners are commonly utilized in vehicles. One disadvantage with such air fresheners is that the card is moist, and can leak or leach, leaving a stain on other surfaces, such as dashboards. The plastic envelope and the suspending loop act to resist contact between the card, and other surfaces. Another disadvantage with such air fresheners is that they are aesthetically displeasing. Another disadvantage with such air fresheners is that they have a more pronounced and immediate scent release, releasing a majority of the scent in the first few days of use.

Another common type of air freshener has a rigid disc-shaped shell or canister with a scented disc or gel inside. The shell can include an adhesive strip to stick or adhere the shell to a surface. One disadvantage with such air fresheners is that removal of the shell often leaves a residue of the adhesive on the surface, which is aesthetically displeasing. In addition, the scented material can leak and harm the surface.

Some disadvantages of common air fresheners include 1) rapid scent loss or lack of longevity; 2) non-linear or inconsistent scent release over time; and 3) risk of staining. Some air fresheners disperse their scent too rapidly, thus losing effectiveness over time, and not lasting as long as desired. Some air fresheners quickly or rapidly disperse their scent after activation, and then slowly release scent, or release little scent, thereafter. Some air fresheners include materials that can leak and stain.

Another disadvantage with some air fresheners is that they include a non-solid and non-liquid material, or a jelly-like material, that must be contained in some type of container because the jelly is flowable. The material can become dried and cracked over time, presenting an aesthetically displeasing appearance. Again, the scented material can leak and damage surfaces.

SUMMARY OF THE INVENTION

In light of the problems and deficiencies inherent in the prior art, it has been recognized that it would be advantageous to develop an air freshener that is more aesthetically pleasing. In addition, it has been recognized that it would be advantageous to develop an air freshener that is easily located or positioned without marring or otherwise damaging other surfaces, and comfortably touched or handled on a daily basis. In addition, it has been recognized that it would be advantageous to develop an air freshener that can last for a desired length of time, such as 30 days, and that can provide for both a constant scent release and, through a simple physical act such as squeezing the air freshener, supplementary bursts of scented air as needed.

In accordance with the invention as embodied and broadly described herein, the present invention provides an air freshener device with a deformable and resilient open cell polyurethane foam body that is interspersed with a scent material. The foam body can be enclosed by a flexible cover, which completely surrounds and conforms to the foam body, and which may be provided with one or more through holes which allow for the passage of air between the foam body and the surrounding atmosphere. The scent material interspersed within the foam body can be dispersed into the immediate and surrounding environment through the holes in the flexible cover. The deformable foam body is compressible under an applied force, which serves to force scent-laden air from the air freshener device into the immediate surroundings. Upon removal of the applied force, the deformable foam body is substantially returnable to an original configuration.

In accordance with one aspect of the present invention, the deformable body can be a coherent elastomer having a free-standing, self-supported, three-dimensional shape, similar to that of a sports ball. Furthermore, the flexible cover can include one or more graphics or indicia formed on its exterior surface to allow the air freshener to serve as a multi-use promotional device.

In accordance with another aspect of the present invention, the fabric cover may be given a non-porous lining to prevent inadvertent leaking or escaping of the scent material from the mantle layer or premature drying of the scent material due to excessive contact with the outside atmosphere.

In yet another embodiment of the present invention, an elastomeric core may be disposed in the air freshener device, such that the foam body forms a mantle layer surround the elastomeric core.

The present invention also provides a method for imparting a burst of scented air into an immediate and surrounding environment, which can include obtaining a deformable, resilient air freshener device having a foam body and a scent material interspersed within the foam body which is capable of diffusing out of the foam, squeezing the air freshener device to expel a burst of scented air from the foam body, and finally releasing the air freshener device to allow the foam body to expand and draw air back into the foam to come into contact the scent material.

Additional features and advantages of the invention will be apparent from the detailed description which follows, taken in conjunction with the accompanying drawings, which together illustrate, by way of example, features of the invention.

BRIEF DESCRIPTION OF THE DRAWINGS

The present invention will become more fully apparent from the following description and appended claims, taken in conjunction with the accompanying drawings. Understanding that these drawings merely depict exemplary embodiments of the present invention they are, therefore, not to be considered limiting of its scope. It will be readily appreciated that the components of the present invention, as generally described and illustrated in the figures herein, could be arranged and designed in a wide variety of different configurations. Nonetheless, the invention will be described and explained with additional specificity and detail through the use of the accompanying drawings in which:

DETAILED DESCRIPTION OF EXEMPLARY EMBODIMENTS

The following detailed description of exemplary embodiments of the invention makes reference to the accompanying drawings, which form a part hereof and in which are shown, by way of illustration, exemplary embodiments in which the invention may be practiced. While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

The following detailed description and exemplary embodiments of the invention will be best understood by reference to the accompanying drawings, wherein the elements and features of the invention are designated by numerals throughout.

The present invention describes an aromatherapy puffer ball, as well as a method of using an aromatherapy puffer ball to provide a burst of scented air to change the olfactory characteristics of the immediate and surrounding environment.

The present invention provides several significant advantages over prior related air fresheners, in that it is more aesthetically pleasing, can easily located or positioned without marring or otherwise damaging other surfaces, and can be comfortably touched or handled on a daily basis. Additionally, the air freshener that can be configured to last for a desired length of time, such as 30 days, while providing for both a constant scent release as well as supplementary bursts of scented air as needed.

Each of the above-recited advantages will be apparent in light of the detailed description set forth below, with reference to the accompanying drawings. These advantages are not meant to be limiting in any way. Indeed, one skilled in the art will appreciate that other advantages may be realized, other than those specifically recited herein, upon practicing the present invention.

Figure 1:
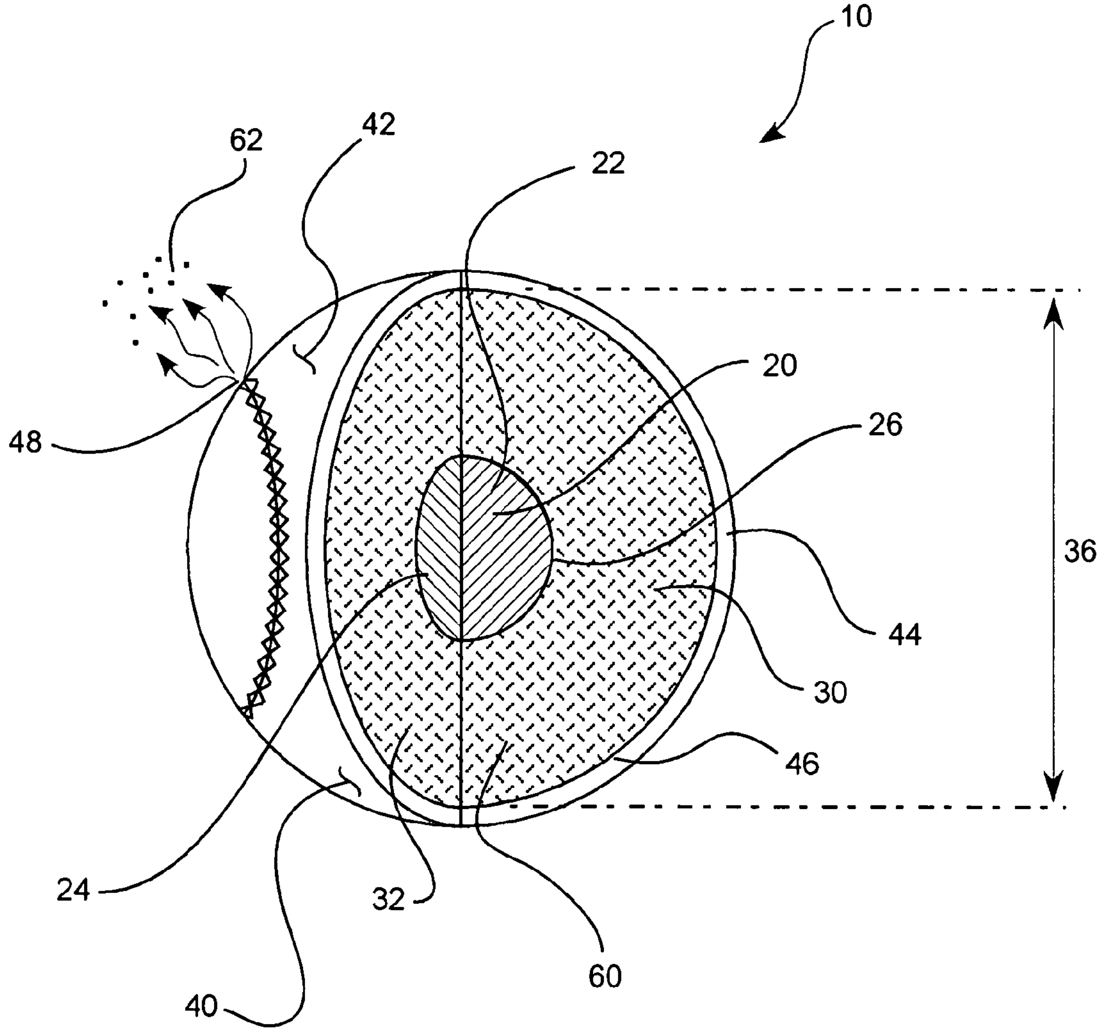
FIG. 1 is a cut-away sectional view of an air freshener in accordance with one embodiment of the present invention.

With reference to FIG. 1, illustrated is an air freshener or scent device, indicated generally at 10, in accordance with the present invention is shown for providing a desired and/or aesthetically pleasing scent, fragrance, aroma or neutralizing agent. Air fresheners are one example of a field that can benefit from the present invention. The air freshener can be used in bathrooms, wash closets, vehicles, offices, bedrooms, etc. The desired scent can include, for example, floral, fruit, vanilla, berry, pine, etc. In accordance with one aspect of the present invention, the air freshener 10 can include a deformable and resilient body having an elastomeric core 20 surrounded by a mantle layer 30 enclosed by a flexible cover 40. Scent material, such as scented oil, can be interspersed in the core 20 and/or the mantle 30. Both the elastomeric core 20 and the mantle layer 30 can be elastic and coherent. Thus, the air freshener body can be compressible under an applied force, and substantially returnable to an original configuration upon removal of the applied force.

In this way, the present invention advantageously provides for an air freshener that protects and separates the scented substance from adjacent surfaces. In contrast, many other air fresheners include warnings to avoid contact with foreign surfaces or objects because the scent material can cause damage to these adjacent or nearby surfaces.

The elastomeric core 20 may be comprised of a polymer gel, otherwise known as a polymer gel core 22. It has been found that the polymer gel provides desired characteristics of aesthetics, flexibility, longevity, substantially constant scent release, and containment. In accordance with another aspect of the present invention, the polymer gel core 22 can have a freestanding, self-supported, three-dimensional shape that does not significantly change as the scent is released.

In another embodiment, the elastomeric core 20 may be comprised of a thermoplastic rubber, otherwise known as a TPR core 24. It has been found that the thermoplastic rubber provides desired characteristics of aesthetics, flexibility, longevity, but without the capability for scent storage and scent release. In accordance with another aspect of the present invention, the TPR core 24 can have a freestanding, self-supported, three-dimensional shape that does not significantly change as the scent is released.

The elastomeric core 20, whether it is a polymer gel core 22, a TPR core 24 or another embodiment of the elastomeric core, is surrounded by a mantle layer 30, which can include a polyurethane material and can further include an open-cell polyurethane foam matrix 32. The mantle layer 30 can also include a viscoelastic foam material (not shown). The polyurethane foam matrix has a substantially open-celled construction that allows for the passage and diffusion of scent material 60 or scent molecules, generally shown as 62, within the foam matrix. The polyurethane foam matrix 32 provides desired characteristics of aesthetics, flexibility, longevity, substantially constant scent release, and containment. In accordance with another aspect of the present invention, the polyurethane foam matrix can have a freestanding, self-supported, three-dimensional shape that does not significantly change as the scent is released.

While in one embodiment of the present invention the elastomeric core 20 and the mantle layer 30 are configured as concentric spheres, it is not a requirement for the mantle layer

30 to assume the same general shape as the elastomeric core 20. For instance, the elastomeric core 20 may have a spherical shape, while the mantle layer 30 which surrounds the core may have a bulbous, semi-bulbous, semi-spherical, tear-drop, oval, oblong, etc. outer design. In accordance with one aspect of the present invention, the elastomeric core 20 is positioned substantially in the center of the mantle layer 32. In another aspect of the present invention the polymer gel core 22 and the polyurethane foam matrix 32 connect through a gel/foam interface 26 which allows for the passage of scent material 60 or scent molecules 62 from the polymer gel core into the polyurethane foam matrix 32.

A flexible cover 40 surrounds and encloses the mantle layer 30 and serves to contain the polyurethane foam matrix 32 while providing a comfortable contact surface 42 for handling by the user. The flexible cover 40 conforms to the surface of the mantle layer 30 and assumes the same general shape as the polyurethane foam matrix 32. The flexible cover 40 adheres to the mantle layer 30 and deforms with the deformable and resilient body of the air freshener 10 when it is compressed by an applied force. In accordance with one aspect of the present invention, the flexible cover 40 may be attached or bonded to the mantle layer 30 by any means commonly known in the art, including but not limited to gluing, adhesive, thermal bonding, etc. In another embodiment the flexible cover 40 may simply surround and enclose the mantle layer 30 by means of a tight mechanical fit, and may not be chemically or thermally bonded to the mantle layer in any way. Furthermore, the flexible cover 40 can include one or more graphics or indicia (not shown) formed on its exterior contact surface 42 to allow the air freshener to serve as a multi-use promotional device.

Figure 2:
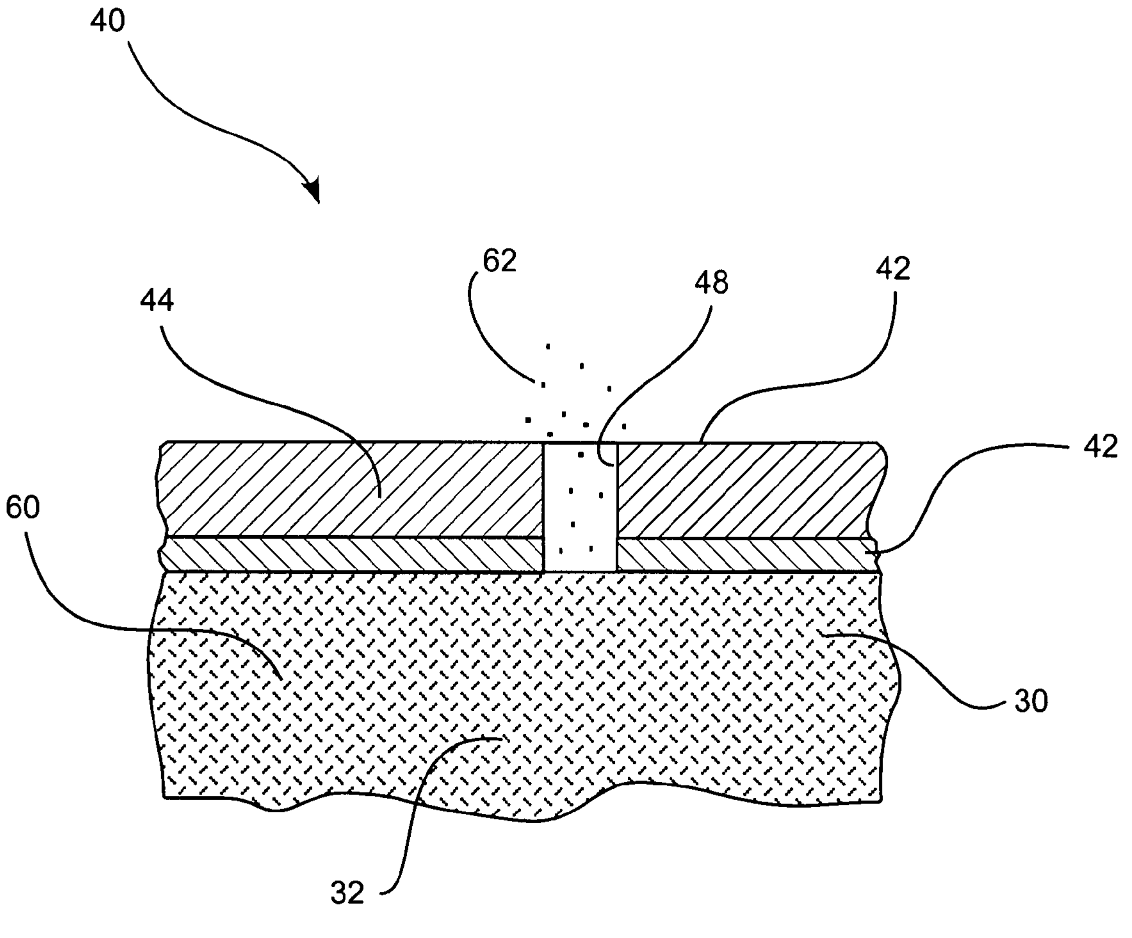
FIG. 2 is a detailed cross-sectional of the air freshener shown in FIG. 1.

As illustrated in FIG. 2, the flexible cover 40 comprises a fabric shell 44 with a contact surface 42 which is pleasing to the touch of the user. According to one aspect of the present invention, the fabric shell 44 is made from a smooth and flexible polyester fabric such as Lycra™ or Spandex™. In another embodiment the fabric shell 44 is comprised of a polyester fleece that can be soothing to the touch. At least one small hole 48 is located in the fabric shell 44 that serves to place the mantle layer 30 in fluid communication with the outside air, and which allows scent-laden air to pass from the mantle 30 to the surrounding atmosphere. With the air freshener of the present invention in a resting and undisturbed state, small amounts of scent molecules, generally depicted at 62, are able to diffuse out of the polyurethane foam matrix 32, through the hole 48 and into the surrounding environment. The amount of diffusion depends entirely on the size and quantity of the hole or holes 48 in the flexible cover 40. Moreover, the quantity and size of the holes 48 in the flexible cover 40 may be varied to allow different embodiments of the present invention to give off scent at different rates, and also may be incorporated into another feature of the air freshener, such as the stitching in the fabric shell 44 resulting from two or more flexible cover or fabric segments being sewn together around the mantle layer 30 of the air freshener. While it is likely that many embodiments of the present will have a plurality of holes 48, according to one aspect of the present invention, there may be only one hole 48 in the fabric shell 44 to allow the passage of scent molecules into the surrounding air.

It is one object of the present invention that from time to time the user of the present invention may increase the strength of the fragrance in his or her immediate vicinity beyond the amount which diffuses naturally through the small holes 48 in the cover 40 of the air freshener. This can be accomplished by squeezing the deformable and resilient body of the air freshener 10. Scent molecules 62 saturate the pockets of air entrained by the polyurethane foam matrix 32. When the deformable and resilient body 10 is compressed by an applied force, the air that is contained within the polyurethane foam matrix 32 is expelled out of the holes 48 into the surrounding atmosphere. Moreover, when the applied force is later released the polyurethane foam matrix 32 springs back into its original shape and volume, creating a natural vacuum which draws fresh air back through the holes 48 and into the mantle layer 30 to extract additional scent molecules 62 out of the scent material 60 embedded within the polyurethane foam matrix 32. This mechanism allows for the repeated and controlled release of a burst of scent molecules 62 into the surrounding environment.

In another aspect of the present invention an inner liner 46 is placed between the fabric shell 44 and the mantle layer 30. The inner liner 46 is a non-porous layer that serves as a buffer between the polyurethane foam matrix 32 and the fabric shell 42 to resist the release of scent. The inner liner 46 may be made from a non-porous material such as thermoplastic polyurethane ("TPU"). At least one small hole 48 will also be placed in this inner liner 46 that is aligned with the hole in the fabric shell, forming a through-hole in the flexible cover 40 from the contact surface 42 to the mantle layer 30.

The inner liner 46 serves to limit the amount of scent molecules 62 which diffuse away from the mantle layer 30 to those which pass through the hole or holes 48 in the flexible cover 40. It is likely that a cloth shell 44 made from a polyester fabric such as Lycra™ or Spandex™ is porous enough that a significant amount of scent molecules 62 may simply pass through the material comprising the fabric shell. This inadvertent passage may allow scent molecules 62 to prematurely diffuse from the mantle layer 30 causing it to loose its scent generating capabilities too soon. Moreover, fresh air may also pass through the fabric shell in the other direction, into the mantle layer. This could result in premature drying of the scent material due to excessive contact with the outside atmosphere. Adding the inner liner 46 prevents the unwanted migration of scent molecules 62 away from the mantle layer 30 or fresh air into the mantle layer, allowing the air freshener 10 to remain active longer.

In another aspect of the present invention the inner liner 46 also serves to contain scent material 60 which may migrate through the polyurethane foam matrix 32 and prevent it from escaping the mantle layer 30 or from otherwise coming into contact with the fabric shell 40. In one aspect of the present invention the scent material, which is interspersed within the polyurethane foam matrix 32 and/or the polymer gel core 22, is a scented oil or similar carrier product that is able to migrate through the open celled structure of the polyurethane foam matrix 32. The scented oil may be contained with the deformable and resilient body; otherwise it may stain or mar the fabric shell 44 or even soil articles in the surrounding environment. Thus the flexible cover 40 may be given a non-porous lining 46 to prevent inadvertent leaking of the scent material 60 from the mantle layer 30.

According to one aspect of the present invention, the polymer gel core 22 and the polyurethane foam matrix 32 may be combined to form a composite scent portion 36 of the air freshener which is used to first store and second deliver the desired scent 62 to the surrounding air. The polymer gel core 22 and the polyurethane foam 32 may have a scent material 60 of the desired scent interspersed therein. The term "scent material" is used broadly herein to refer to a material that has a scent that can be discernable or smelled, or even a neutralizing agent. Thus, the scent can be an ascertainable smell used to cover other scents, or a neutral agent that eliminates odors or provides a fresher atmosphere. Moreover, the scent material 60 can be interspersed into the composite scent portion 36 of the air freshener, including either the polyurethane foam matrix 32 or the polymer gel core 22, after the foam matrix or the gel core have been formed, as it may be desirable to wait until after the polyurethane material has aged for a predetermined time before interspersing the scent material into the foam matrix or the gel core.

As the mantle layer 30 can completely surround the core, the scent material disperses or diffuses out of the polymer gel core 22, across the gel/foam interface 26, and into the polyurethane foam matrix 32. From there the scent disperses or diffuses out of the polyurethane foam matrix 32 into the air or atmosphere, by way of the holes 48 in the flexible cover 40, where it can be detected, or where it can provide a discernable scent. The scent material 60 can be high in volatile notes, or has high volatility and can vaporize or evaporate at low temperatures. The scent material 60 can include a scented oil. For example, suitable scent material can include pine, berry, vanilla, apple, coconut, cherry, pina colada, etc.

The polymer gel core 22 can be elastic and coherent and deformable under normal conditions. The polymer gel core 22 can be flexible and resilient, such that the body or gel can compress under an applied force, but can substantially return to its original configuration upon removal of the applied force. The polymer gel core 22 can have a freestanding, self-supported, three-dimensional shape. Thus, the polymer gel core can be consistent or solid enough to support or maintain its shape in a freestanding manner without a container. The three-dimensional shape can be any desired shape. The polymer gel core 22 can be considered a solid material that is elastic and coherent, and thus flexible and capable of being deformed, but without being flowable. Thus, the polymer gel core 22 may have a sufficiently high molecular weight, and/or a sufficiently high viscosity, so that it is a non-flowable gel. In addition, the polymer gel core 22 can be considered as stable. Thus, the polymer gel can be bendable, but otherwise substantially maintains its form. Thus the polymer gel core 22 can be characterized as a polymeric material in the glass state with substantially no macroscopic flow. The polymeric material can have a glass transition temperature greater than approximately 110° F. As a result, the polymer gel core 22 can retain its gel-like characteristic over time, without drying or cracking, and without becoming hard or brittle.

In one embodiment, the polymer gel core 22 can include a polyurethane material or can be a polyurethane gel. The gel can be formed by combining a polyurethane material with a scented oil. Surprisingly, it has been found that such a combination provides a desired scent, but without staining or substantially leaking onto a surface. As such, the polymer gel core does not undergo a physical change, such as drying out or cracking, as the scent material diffuses away into mantle layer of polyurethane foam.

In some embodiments, a scented oil and a polymerizable monomer can be combined, along with optional initiators or other reactants. Isocyanate reaction polymers have shown good results in connection with the present invention. For example, the polymer gel core 22 and scent material can be a urethane polymerization product of combining a scented oil with a polyether polyol, and then with a diphenylmethane diisocyanate (MDI) prepolymer. Therefore, in some embodiments, the scent material can be a scented oil which participates in the polymerization reaction between polymerization reactants. For example, essential oils such as terpenes and the like can be mixed with polymerization reactants, or even in place of some reactants. Without being bound by any particular theory, it is thought that at least some of the reduction or elimination in residue in the devices of the present invention result from at least partial replacement of mineral oils and/or polyols with scented oils such as those listed herein. Other suitable isocyanates can include, but are not limited to, tolylene diisocyanates, methylene diphenyl isocyanates, hexamethylene diisocyanates, prepolymers thereof, and the like. Those skilled in the art will recognize various other isocyanate reaction polymers, i.e. polyurethanes, which can be suitable for use in connection with the present invention.

Alternatively, the polymer gel core 22 can include silicone, diffused polyurethane, polyvinylchloride (PVC), ethylene vinyl acetate (EVA), thermoplastic polyurethane (TPU), a polymer encapsulation fragrance delivery platform (PolyIFF®), thermoplastic elastomer (TPE), polypropylene, ethylene/methacrylic acid (E/MAA) copolymer, in which the MAA groups have been partially neutralized with lithium ions (Surlyn® Dupont), etc.

As a general guideline, the polymer gel core 22 can be formed of an elastomer such as, but not limited to, urethanes (including polyester and polyether polyol/isocyanate polymerization products), polyacrylates, polybutadienes, ethylene propylene elastomers, silicones, natural and synthetic rubbers, styrene/butadiene block copolymers, and the like. In some embodiments, the polymer gel core can be formed of a thermoplastic elastomer. Thermoplastic elastomers can be block copolymers such as polyurethanes, polyamides, copolyesters, and styrene-butadiene-styrene polymers. Other thermoplastic elastomers can be elastomer/thermoplastic blends such as ethylene-propylene-diene monomer in an isotactic polypropylene phase or nitride rubber dispersed in a PVC phase. As used herein, "thermoplastic elastomer" refers to an elastomer which can be heated and processed like thermoplastic materials. Specifically, a thermoplastic elastomer can be heated to a melted or flowable state and then cooled, resulting in reformation of cross-linking and subsequent coherency without a substantial change in mechanical properties such as strength, flexural modulus, elastic modulus, etc.

The composite scent portion 36 of the air freshener 10, previously described as the polymer gel core 22 combined with the polyurethane foam matrix 32, can be used to store a scent material 60 of the desired scent interspersed therein and to deliver the desired scent molecules 62 to the surrounding air. The shape and size of the scent portion 36 can be configured to determine the amount or quantity of scent stored by the air freshener 10. For example, the scent portion 36 can assume any shape. The scent portion 36 can be bulbous, semi-bulbous, semi-spherical, teardrop, oval, oblong, etc. However, in a preferred embodiment the scent portion assumes the size and shape of a small round sports ball, similar to that of a baseball. It will be appreciated that an air freshener 10 with a scent portion 36 of this size has several advantages. A baseball-sized air freshener 10 is easily manipulated with one hand by most adult users, allowing individuals to squeeze the object with little effort. Moreover, the air freshener 10 could easily be transportable in one's coat pocket or in a purse, allowing the user to affect the smell of the immediate surroundings wherever he or she goes. Furthermore, an air freshener 10 the size of a baseball may be easily stored an the average shelf, desktop or window sill. All of these factors and characteristics can be combined in a preferred embodiment to create an air freshener that is easy to use and is both convenient to store and to carry.

It will be appreciated that the air freshener 10 can be configured or shaped to appear as various different objects. The shape or configuration of the scent device 10 can provide an aesthetic pleasing appearance. For example, the shape and appearance of the scent device can differ significantly from traditional air fresheners. Other air fresheners often have a utilitarian appearance, such as cans or canisters, while others have an appearance associated with air fresheners. Thus, the air freshener 10 of the present invention can have a shape and appearance not typically associated with air fresheners. Furthermore, various graphics or indicia can also be provided on the flexible cover 40 of the air freshener 10. Such indicia can be molded or printed on the contact surface 42 of the air freshener 10.

In addition, one or more air fresheners can be provided as collectibles. In accordance with one aspect of the present invention, the air freshener 10 can be shaped, configured or printed to indicate a commemorative event, such as a business anniversary, a holiday, etc. As another example, a plurality of different air fresheners can be provided in families or groups, with each air freshener having a different size, shape, and/or color. As another example, a plurality of different air fresheners can be provided with different shapes that fit together or coordinate to form another object. The air fresheners can include mating protrusions and recesses, so that the air fresheners can be fitted together to form another object or design.

Figure 3:
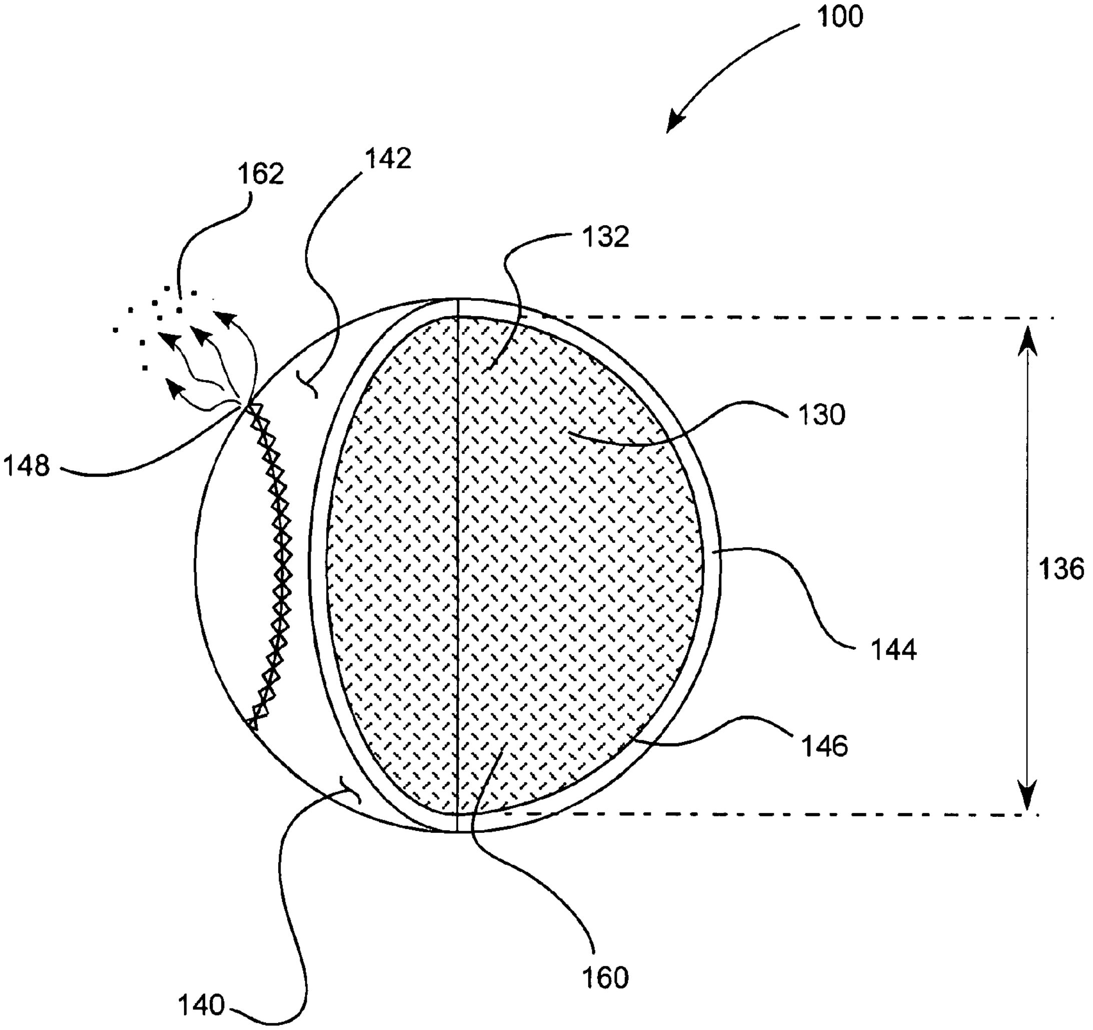
FIG. 3 is a cut-away sectional view of an air freshener in accordance with another embodiment of the present invention.

As illustrated in FIG. 3, a deformable, resilient air freshener device, indicated generally at 100 is shown in accordance with another embodiment of the present invention for providing a desired and/or aesthetically pleasing scent, fragrance, aroma or neutralizing agent. The air freshener can be similar in many respects to the air freshener 10 described above and shown in FIGS. 1-2. Additionally, the air freshener 100 can have a foam body 130 with a scent material 160 interspersed in the foam body.

The foam body 130 can include a polyurethane material and can be an open-cell polyurethane foam matrix 132 as described above. The foam body can also a viscoelastic foam material (not shown). The foam body can be deformable and can compress under an applied load. The foam body can be formed in a variety of shapes and sizes as previously described. In one aspect, the foam body can be a sphere or ball that is sized and shaped to be held in the hand of a user.

The scent material 160 can be a scented oil combined with a polymeric material, such as polyurethane, as described above. The scented material can diffuse out of the foam body 130 over time to provide an pleasing aromatic smell to an area nearby the foam body. Additionally, the foam body can be compressed, and when compressed, the scent material can diffuse out of the foam body at a higher rate to provide a burst of scented air to the area near the foam body.

The scent material 160 can be interspersed into the foam body 130 after formation of the foam body. In the case where the foam body is a polyurethane material, the polyurethane material can be allowed to cure to form the foam body and then the scented material can be injected into the foam body. Additionally, the polyurethane material can be allowed to age after cure for a predetermined time prior to injection of the scent material. After the predetermined aging time is completed, the scent material can be injected into the foam body. Advantageously, injecting the scent material into the foam body after formation reduces burn off of the scented oil or scent material during hot injection molding processes, and aging polyurethane foam materials reduces the unpleasant odors naturally associated and emanating from newly formed polyurethane bodies.

As described more completely above, a flexible cover 140 can surround and enclose the foam body 130, conforming to the surface of and assuming the same general shape as the underlying foam body. The flexible cover also adheres to the foam body and deforms with it when the air freshener 100 is compressed by an applied force. In accordance with one aspect of the present invention, the flexible cover can be attached or bonded to the foam body by any means commonly known in the art, including but not limited to gluing, adhesive, thermal bonding, etc. In another embodiment the flexible cover can simply surround and enclose the foam body by means of a tight mechanical fit, and may not be chemically or thermally bonded to the foam body in any way.

The flexible cover 140 may further comprise a fabric shell 144 with a contact surface 142 which is pleasing to the touch of the user. The fabric shell can be made from a smooth and flexible polyester fabric such as Lycra™ or Spandex™. In another embodiment the fabric shell can be comprised of a polyester fleece that can be soothing to the touch. At least one small hole 148 can located in the fabric shell that serves to place the foam body 130 in fluid communication with the outside air. With the air freshener of the present invention in a resting and undisturbed state, small amounts of scent molecules, shown generally at 162, are able to diffuse out of the polyurethane foam matrix 132, through the hole 148 and into the surrounding environment. The amount of diffusion depends entirely on the size and quantity of the hole or holes 148 in the flexible cover 140. The quantity and size of the holes 148 in the flexible cover 140 may be varied to allow different embodiments of the present invention to give off scent at different rates. While it is likely that many embodiments of the present will have a plurality of holes 148, according to one aspect of the present invention, there may be only one hole 148 in the fabric shell 144 to allow the passage of scent molecules into the surrounding air.

In another aspect of the present invention an inner liner 146 can be placed between the fabric shell 144 and the foam body 130. The inner liner is a non-porous layer that serves as a buffer between the foam body and the fabric shell to resist the release of scent. The inner liner may be made from a non-porous material such as thermoplastic polyurethane ("TPU"). At least one small hole 148 will also be placed in this inner liner that is aligned with the hole in the fabric shell, forming a through-hole in the flexible cover 140 from the contact surface 142 to the foam body 130.

Figure 4:
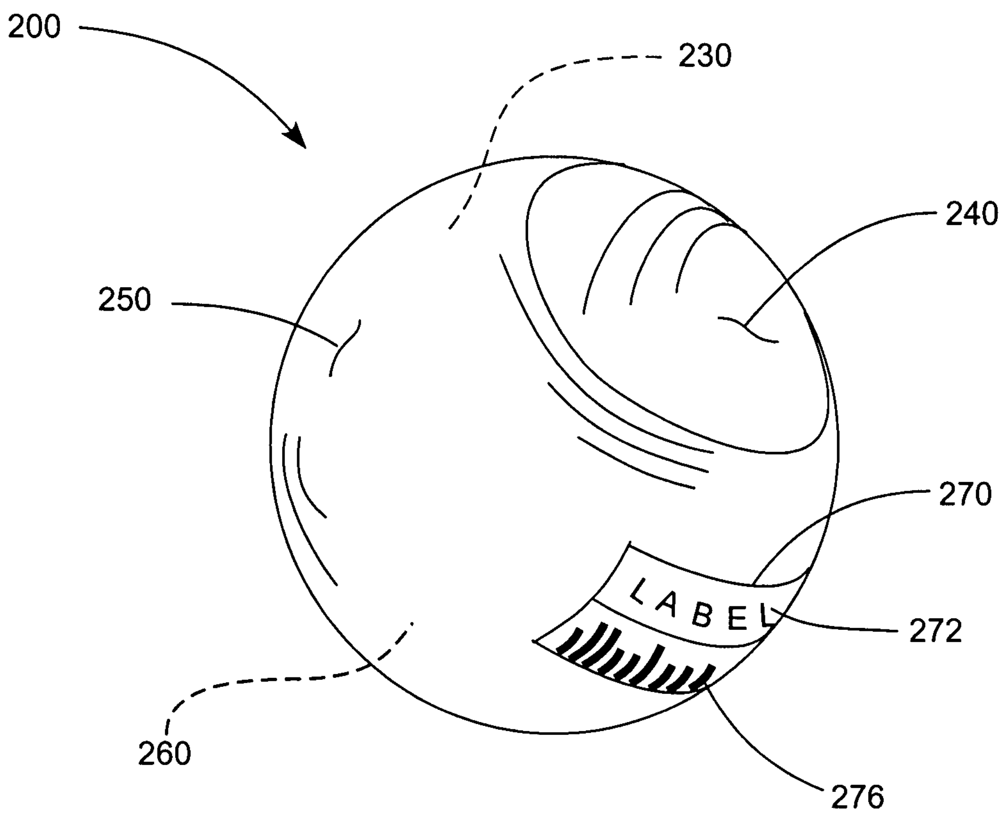
FIG. 4 is a perspective view of the air freshener of FIG. 1 or 3 disposed in a shrink film container.

Referring to FIG. 4, an air freshener 200 is shown with an additional film layer of shrink material 250, partially enclosing the air freshener 200. The shrink material can be a heat sensitive polymeric material that shrinks in when heated, as known in the art. The shrink material or film can be wrapped around the foam body and then tightly shrunk against the outer skin or covering of the foam body. In one aspect the shrink film can enclose approximately 75% of the surface area of the foam body to form a container or packaging system about the foam body.

Figure 5:
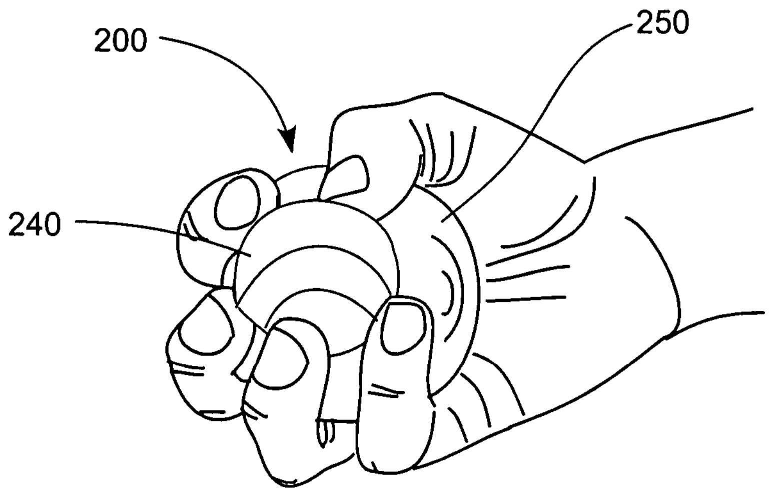
FIG. 5 is a perspective view of the air freshener of FIG. 1 or 3 compressed in the hand of a user.

Advantageously, the shrink film 250 allows the consumer or user of the air freshener 200 to test the scent of the air freshener by squeezing the air freshener without touching or soiling the flexible cover 240, as shown in FIG. 5. Thus, the shrink material can be a flexible material that can deform under an applied load and allow a user to compress the foam body contained within the shrink film thereby allowing a demonstrative burst of scented air from the portion of the surface area of the foam body not enclosed in the container. In this way, the film of flexible shrink material can reduce exposure of the flexible cover 240, foam body 230 and the scent material 260 contained in the foam body to reduce inadvertent contact with foreign materials, such as a consumer's hand or other scented air fresheners that may be stacked adjacent one another. Advantageously, this reduces contamination of the foam body and scent material from other adjacent air fresheners and preserves the original scent for use by a purchasing consumer. Additionally, the packaging layer of shrink film can at least partially contain the scented material within the foam body, thereby slowing the dispersal rate of the scent material while the foam body is packaged within the shrink film.

The film of flexible shrink wrap material 250 can also include indicia or a label 270 with indicia 272 formed thereon. In this way, the film of flexible material can include packaging information such as a trademark or name of the air freshener, manufacturing vitae, care instructions, a bar code 276, and the like.

The present invention can also include a method for providing a burst of scented air into the immediate, surrounding environment, which comprises obtaining a deformable, resilient air freshener device having a foam body and a scent material interspersed within the foam body which is capable of diffusing out of the foam, squeezing the air freshener device to expel a burst of scented air from the foam body, and ultimately releasing the air freshener device to allow the foam body to expand and draw air back into the foam to come into contact the scent material.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

More specifically, while illustrative exemplary embodiments of the invention have been described herein, the present invention is not limited to these embodiments, but includes any and all embodiments having modifications, omissions, combinations (e.g., of aspects across various embodiments), adaptations and/or alterations as would be appreciated by those in the art based on the foregoing detailed description. The limitations in the claims are to be interpreted broadly based on the language employed in the claims and not limited to examples described in the foregoing detailed description or during the prosecution of the application, which examples are to be construed as non-exclusive. For example, in the present disclosure, the term "preferably" is non-exclusive where it is intended to mean "preferably, but not limited to." Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given above.

What is claimed and desired to be secured by Letters Patent is:

1. A deformable, resilient air freshener device, comprising:

an open-cell, polyurethane foam body;

a scent material interspersed in the foam body and being capable of diffusing out of the foam body;

a flexible cover comprising a fabric shell surrounding and conforming to the foam body having at least one hole in the cover to facilitate the release of scent; and the fabric shell having a non-porous inner liner to resist the release of scent.

2. The air freshener device of claim 1, wherein the fabric shell is further comprised of a flexible polyester fabric.

3. The air freshener device of claim 1, wherein the fabric shell is provided with a textured surface.

4. The air freshener device of claim 1, wherein the inner liner is further comprised of thermoplastic polyurethane.

5. The air freshener device of claim 1, wherein the flexible cover comprises a plurality of segments sewn together and wherein the at least one hole in the cover for the release of scent is aligned with the pattern of stitching.

6. The air freshener of claim 1, wherein the flexible cover further includes at least one graphic having indicia formed thereon.

7. The air freshener device of claim 1, wherein the foam body is compressible and the scent material is diffused out of the foam at a higher rate when the foam body is compressed.

8. The air freshener device of claim 1, wherein the scent material is interspersed into the foam body after the foam body is formed.

9. The air freshener device of claim 8, wherein the scent material is interspersed into the foam body after the polyurethane material has aged for a predetermined time.

10. The air freshener device of claim 1, wherein the foam body further comprises an elastomeric core disposed therein and the polyurethane foam body forms a mantle layer surrounding the elastomeric core.

11. The air freshener device of claim 10, wherein the elastomeric core is further comprised of a polymer gel selected from the group consisting of polyurethane, polyacrylate, polybutadiene, ethylene propylene elastomer, styrene/butadiene block copolymer, and mixtures thereof.

12. The air freshener device of claim 10, wherein the elastomeric core is further comprised of a thermoplastic rubber.

13. The air freshener device of claim 1, wherein the scent material is a scented oil.

14. The air freshener device of claim 1, wherein the foam body is a sphere sized to be handheld.

15. The air freshener device of claim 1, further comprising a shrink film enclosing approximately 75% of the surface area of the foam body.

16. The air freshener device of claim 15, wherein the film of flexible shrink material forms a container substantially enclosing the foam body and allowing a demonstrative burst of scented air from the surface area of the foam body not enclosed in the container when the foam body is compressed within the shell flexible shrink wrap.

17. The air freshener of claim 15, wherein the film of flexible shrink wrap material further includes a label having indicia formed thereon.

18. A deformable, resilient air freshener device, comprising:

an open-cell, polyurethane foam body;

a scent material interspersed in the foam body and being capable of diffusing out of the foam body;

a flexible cover surrounding and conforming to the foam body having at least one hole in the cover to facilitate the release of scent; and a shrink film enclosing approximately 75% of the surface area of the foam body.

19. The air freshener device of claim 18, wherein the film of flexible shrink material forms a container substantially enclosing the foam body and allowing a demonstrative burst of scented air from the surface area of the foam body not enclosed in the container when the foam body is compressed within the shell flexible shrink wrap.

20. The air freshener of claim 18, wherein the film of flexible shrink wrap material further includes a label having indicia formed thereon.

21. The air freshener device of claim 18, wherein the flexible cover further comprises a fabric shell.

22. The air freshener device of claim 21, wherein the fabric shell is further comprised of a flexible polyester fabric.

23. The air freshener device of claim 21, wherein the fabric shell is provided with a textured surface.

24. The air freshener device of claim 21, wherein the fabric shell has a non-porous inner liner to resist the release of scent.

25. The air freshener device of claim 24, wherein the inner liner is further comprised of thermoplastic polyurethane.

* * * * *